United States Patent [19]

Shimoni

[11] Patent Number: 4,616,333

[45] Date of Patent: Oct. 7, 1986

[54] DATA CORRELATION SYSTEM

[75] Inventor: Yair Shimoni, Jerusalem, Israel

[73] Assignee: Elscint, Ltd., Haifa, Israel

[21] Appl. No.: 617,554

[22] Filed: Jun. 5, 1984

[51] Int. Cl.[4] ............................................. G06G 7/19
[52] U.S. Cl. ................................... 364/819; 364/417;
364/728
[58] Field of Search ............... 364/819, 820, 728, 415,
364/417; 128/702, 698; 324/77 G; 382/30, 42

[56] References Cited

U.S. PATENT DOCUMENTS

| | | | |
|---|---|---|---|
| 4,170,992 | 10/1979 | Dillman | 364/417 X |
| 4,211,237 | 7/1980 | Nagel | 364/417 X |
| 4,349,880 | 9/1982 | Southgate et al. | 364/819 |
| 4,471,453 | 9/1984 | Ney et al. | 364/819 X |

Primary Examiner—Joseph Ruggiero
Attorney, Agent, or Firm—Sandler & Greenblum

[57] ABSTRACT

A pseudo correlation system and method for determining matches between data defined shapes and templates by obtaining a pseudo correlation value without a successivity of multiplications or determining square roots.

30 Claims, 3 Drawing Figures

TEMPLATE

ACQUIRED DATA I

ACQUIRED DATA II

DATA CORRELATION SYSTEM

FIELD OF THE INVENTION

This invention is related to data processing of data streams and, more particularly for use in matching patterns in acquired data streams with predetermined or "template" patterns.

BACKGROUND OF THE INVENTION

Among the many data processing methods that are used with data streams is "pattern matching". This process "relates" or matches acquired data to a predetermined pattern or template. Some matching techniques use mathematical or geometrical measurements of the data pattern and the template to yield numerical values of the degree of matching. These matching techniques are sometimes referred to as "correlation methods" for matching. These correlation methods employ theorems of Statistics Theory.

Examples of correlation and the use of correlation are found in such divergent fields as medical imaging for diagnostic purposes and military surveillance imaging for the purpose of locating enemy units, communications (especially for error detection and correction, and for the detection of specific signals), etc.

Correlation methods and systems are also used, for example, to determine the location of R-waves in an Electro-Cardiogram (ECG or EKG) trace and to classify the heart beat (according to the shape of the so-called QRS shape of the ECG trace) into one of several types.

A popular and widely studied correlation technique in use is known as "linear correlation". This is a statistical technique wherein correlation is determined by the value of the criteria R; where:

$$R = \frac{\sum_{i=1}^{N}(X_i - \overline{X}) \cdot (Y_i - \overline{Y})}{\left(\sum_{i=1}^{N}(X_i - \overline{X})^2 \cdot \sum_{i=1}^{N}(Y_i - \overline{Y})^2\right)^{\frac{1}{2}}} = \tag{1}$$

$$\frac{\overline{XY} - \overline{X} \cdot \overline{Y}}{(VAR(X) \cdot VAR(Y))^{\frac{1}{2}}}$$

where Y is the template data, X is the acquired data, $\overline{Y}$ is the arithmetic mean of the template and $\overline{X}$ is the arithmetic mean of the acquired data; $R\epsilon[1,-1]$—that is R has a value between $+1$ and $-1$ inclusive. It has a value of $+1$ if the acquired shape and the template shape look alike, and $-1$ if one is an upside down exact match of the other; in these cases one can write for all i:

$$Y_i = aX_i + b \quad \text{(a linear relationship)}$$

and R equals:
  $+1$ if a is larger than 0,
  $-1$ if a is smaller than 0;

The symbols $X_i$ and $Y_i$ denote ordered sets, with i the ordinal index; R has a value of 0 if there is no relationship between the acquired pattern and the template pattern; and VAR is the statistical variation.

A match is usually declared if R or $|R|$ (its absolute or unsigned value) has a value above a predetermined threshold value. This threshold is usually set close enough to 1 (say, 0.85) to avoid spurious matchings, especially if the data is "noisy".

The data being examined is usually a representation of some physical information in the object examined. Due to system limitations and inaccuracies, the same physical information will not necessarily be represented by the same data value if measured repeatedly. These differences are referred to as "noise". The larger the spread of the data values for a given physical information, the noisier the data stream of the measuring system is considered to be. Such "noise" may create a spurious pattern, reminedful of the "template" pattern, it is usually the aim of the correlation (or any matching) method to avoid those spurious patterns.

The linear correlation declares a match according to linear dependency only. The scales can be vastly different between the template and data, and yet R will equal 1. While this is what is needed for some applications, many applications look for a correlation method that recognizes scale as well as shape.

Another problem with this prior art technique is that it requires relatively large amounts of computer time and memory. This is caused by several things; such as:

a. Averages of acquired data are required to provide a fiducial or reference value; which means, it is necessary to calculate averages before computing the correlation value. It also means that all the data values have to be retained in the computer if a correlation factor is calculated for consecutive points. The same is true if for a given point the correlation factor is calculated over a number of data set sizes. In both cases, new means have to be calculated for each change.

b. For each value of i at least two multiplications are required, multiplication being a relatively time consuming computer operation.

c. Square roots are also required which take up more computer time.

Accordingly, with the prior art methods, excessive time is required for the computations, making the use of these prior art correlation methods limited for real-time application.

Scientists in the data processing fields, for example where data processing is done for pattern matching purposes, are always searching for new methods and systems which will decrease the time required for the correlation computations and improve the accuracy of the final results. Accordingly, an object of the present invention is to provide new, faster and improved correlation methods and systems. Herein the new correlation methods are referred to as pseudo correlation since they do not follow the classical prior art correlation methods or systems. A pertinent article on correlation authored by D. I. Barnea and H. F. Silverman appears in Transactions on Computers, 1972.

BRIEF DESCRIPTION OF THE INVENTION

According to one broad aspect of the present invention, a method of determining whether newly acquired data matches some predetermined pattern is provided, said method comprising the steps of:

determining a first set of data $Y_i$ at a plurality of N data points describing the predetermined patterns, and numbering the points therein $Y_i$, with $i=1,2,\ldots,N$;

acquiring a second set of data $X_i$ of at least the same number of data points N from a data acquisition system, said second data set comprising the data at M points from the beginning of the measurement until the data point last acquired;

selecting a subset of data points of the same number N, and numbering the points therein Xi, with i=1, 2 .. . N selecting a fiducial value within said first set and a fiducial value within said subset, calculating a divisor and a dividend from said first data set describing the predetermined pattern and said data sub set describing the acquired pattern, said dividend and said divisor consisting of values obtained by the summations of subtractions using said first data set, said subset along with said selected fiducials, and comparing the quotient obtained using said dividend and said divisor with a threshold level to determine matching.

A feature of the invention uses a dividend that is the summation of the absolute values of the difference between the quantity of the data subset value at each point minus the first data set value at each point and the quantity of the data subset value at the first point minus the first data set value at the first point. The divisor is the sum of the summations of the absolute values of (1) the subset data value at each point minus the subset data value at the first point and (2) the first set data value at each point minus the first set data value at the first point.

The summations above are given by:

$$P = \frac{\sum_{i=1}^{N} |(Xi - X1) - (Yi - Y1)|}{\sum_{i=1}^{N} |Xi - X1| + \sum_{i=1}^{N} |Yi - Y1|} = \quad (2)$$

$$\frac{\sum_{i=1}^{N} |(Xi - Yi) - (Xi - Y1)|}{\sum_{i=1}^{N} |Xi - X1| + \sum_{i=1}^{N} |Yi - Y1|}$$

where: $|V|$ is the absolute unsigned value of V.

Another related feature, includes the steps of:
multiplying the quotient by 2,
subtracting the multiplied quotient from 1, and
comparing the difference with some threshold value to determine matching.

The pseudo-correlation value is given by:

$$r = 1 - 2P = 1 - 2* \frac{\sum_{i=1}^{N} |(Xi - X1) - (Yi - Y1)|}{\sum_{i=1}^{N} |Xi - X1| + \sum_{i=1}^{N} |Yi - Y1|} = \text{etc;} \quad (3)$$

A further related feature of the invention dispenses with the multiplication by 2 and subtraction from 1 and compares the quotient with a threshold value.

Yet another feature of the invention comprises the steps of:

using Y1 and X1 value of each of the data sets, as the fiducial values for these sets, subtracting Y1 from Yi and X1 from Xi at each of the data points of said predetermined shape and said shape being acquired to obtain the differences (Xi−X1) and (Yi−Y1) at each of said data points where data has been acquired, subtracting the said differences at each data point to obtain new differences (Xi−X1)−(Yi−Y1), computing as a divisor the sum of the summations of the absolute values of the differences (Xi−X1) and (Yi−Y1) at each said data points where data has been acquired, computing as a dividend, the summation of the absolute value of (Xi−X1) (Yi−Y1), and obtaining the quotient.

In some applications the template is given before the start of acquisition, while at others a template is constructed from the acquired data, usually during the first part of the acquisition. In some applications the template remains unchanged during the acquisition and comparison process, while in others it is periodically, sporadically or continuously updated. This invention covers all such cases.

In some systems it is preferred to actually compute the values of each data as described above. However, a preferred aspect of the invention calculates the template differences Yi−Y1 and the template's summation of absolute differences Yi−Y1 once for each template.

It is then convenient to define a new set of template data $zi = Yi - Y1$ and $$Z = \sum_{i=2}^{N} |Yi - Y1|.$$

For these values the same quotient and pseudo-correlation that were defined by equation (2) and (3) can be defined as:

$$P = \frac{\sum_{i=2}^{N} |Xi - X1 - Zi|}{\sum_{i=2}^{N} |Xi - X1| + Z} \quad (4a)$$

$$r = 1 - 2* \frac{\sum_{i=2}^{N} |Xi - X1 - Zi|}{\sum_{i=2}^{N} |Xi - X1| + Z} = 1 - 2P \quad (4b)$$

It can be seen that the calculation of the pseudo-correlation is much faster and simpler than that of the linear correlation, because:

A. There are no multiplications involved;
B. There are no square roots involved;
C. The number of data points processed is smaller by 1, as i=1 can be eliminated from all summations;
D. Changing the size of the data set involves no new calculations on the template or the value of X1 (which replaced the mean X which had to be recalculated); and
E. X1 is easily found when changing the data set, compared to a recalculation of X.

It must be noted that the numerical scale 2 and the numerical added 1 transforming equation (2) into equation (3) etc.; are only convenience constants selected so that the pseudo-correlation will have similar properties as those of the linear correlation. This exemplary choice in no way limits the scope of this invention, and as a matter of fact equation (2) is preferrable in terms of computation speed.

The unique properties of the pseudo-correlation of equation (3) or (4), include:

a. If the ordered set Xi differs by a constant from Yi but has the same scale, then r=1.
b. For any set of Xi and any set of Yi, r is between +1 and −1, inclusive.
c. If there is a linear relationship $Xi = aYi + b$ and if: a is larger then 1, then $r = (3-a)/(1+a)$, or if: a is between 1 and 0, then $r=(3a-1)/(a+1)$,
or if: a is smaller than 0, then $r=-1$.

d. For $|a|\to\infty$, $r\to-1$ (i.e. the larger the absolute value of a, the closer r is to $-1$).

Thus, the psuedo-correlation of equations (3) and (4) differs from the linear correlation in several ways, such as:

a. It is sensitive to scale.
b. It is more sensitive to changes (a lower threshold is needed).
c. The set Xi=C has a linear correlation R=0 with any different set Yi, but $r=-1$.
d. A set Xi which relates to Yi in such a way as to evenly cover a circular or annular area in the Z-Y plane has a linear correlation R=0 regardless of the values of Xi and Yi; such sets do not have a definite psuedo-correlation, although r is usually negative.
e. When Yi is a linear set: $Yi=Ai+B$, and Xi is another linear set: $Xi=Ci+D$, then the linear correlation R equals 1, while the pseudo-correlation r equals $1-2*|C-A|/(|C|+|A|)$; thus if C and A have different signs $r=-1$.

The technique described above can be utilized in many different types of correlations or psuedo-correlations, such as:

(a) Multi-template pseudo-correlation. —The speed of the method enables comparing the incoming data stream with several templates to decide which template fits which part of the data stream.

(b) Multi-data pseudo-correlation. —The speed of the method enables parallel comparisons of a template with several data streams.

(c) Multi-dimensional pseudo-correlation or Vector pseudo-correlation. —Assume that the template Y and the acquired data X both are n-dimensional vectors:

$$X=(^1x, ^2x, ^3x, \ldots, ^nx)$$
$$Y=(^1y, ^2y, ^3y, \ldots, ^ny) \quad (5)$$

where the scalars $^jx$, $^jy$, denote the projection of the vectors X and Y along the jth coordinate axis.

The "linear" correlation then is:

$$^nR = \frac{\sum_{i=1}^{N}(Xi-\overline{X})(Yi-\overline{Y})}{\left|\sum_{i=1}^{N}(Xi-\overline{X})^2 \cdot \sum_{i=1}^{N}(Yi-\overline{Y})^2\right|^{\frac{1}{2}}} = \quad (6)$$

$$\frac{XY-N\overline{XY}}{\left|\left(\sum_{i=1}^{N}Xi^2-N\overline{X}^2\right)\cdot\left(\sum_{i=1}^{N}Yi^2-N\overline{Y}^2\right)\right|^{\frac{1}{2}}}$$

where the dot denotes "scalar" multiplication:

$$X\cdot Y = {}^1x^1y + {}^2x^2y + \ldots + {}^nx^ny \quad (7a)$$

$$X^2 = {}^1x^2 + {}^2x^2 + \ldots + {}^nx^2 \text{ etc;.} \quad (7b)$$

The scalar multiplication of a vector with itself ($X^2$) is the familiar length or size of the vector.

The consistent expansion of the present inventive method to several dimensions requires the use of the following equations:

$$^nP = \frac{\sum_{i=2}^{N}||(Xi-X1)-(Yi-Y1)||}{\sum_{i=2}^{N}||Xi-X1|| + \sum_{i=2}^{N}||Yi-Y1||} \quad (8)$$

and $^nr=1-2^nP$, where the symbol $||v||$ is a pseudo-size, (or "norm", in mathmatical language) which replaces the regular vector size.

$$||v|| = |^1v| + |^2v| + |^3v| + \ldots + |^nv| \quad (9)$$

Thus, in order to get a perfect match, ($^nr=1$) both sets, the template and the acquired one, have to be exactly the same in all their projections, thus they must have the same orientation. A different method is needed if shape recognition is required independent of orientation.

BRIEF DESCRIPTION OF THE DRAWINGS

The above mentioned other objects and features of the present invention will be best understood when considered in the light of the following description taken in conjunction with the accompanying drawings, in which.

GENERAL DESCRIPTION

Figure 1:
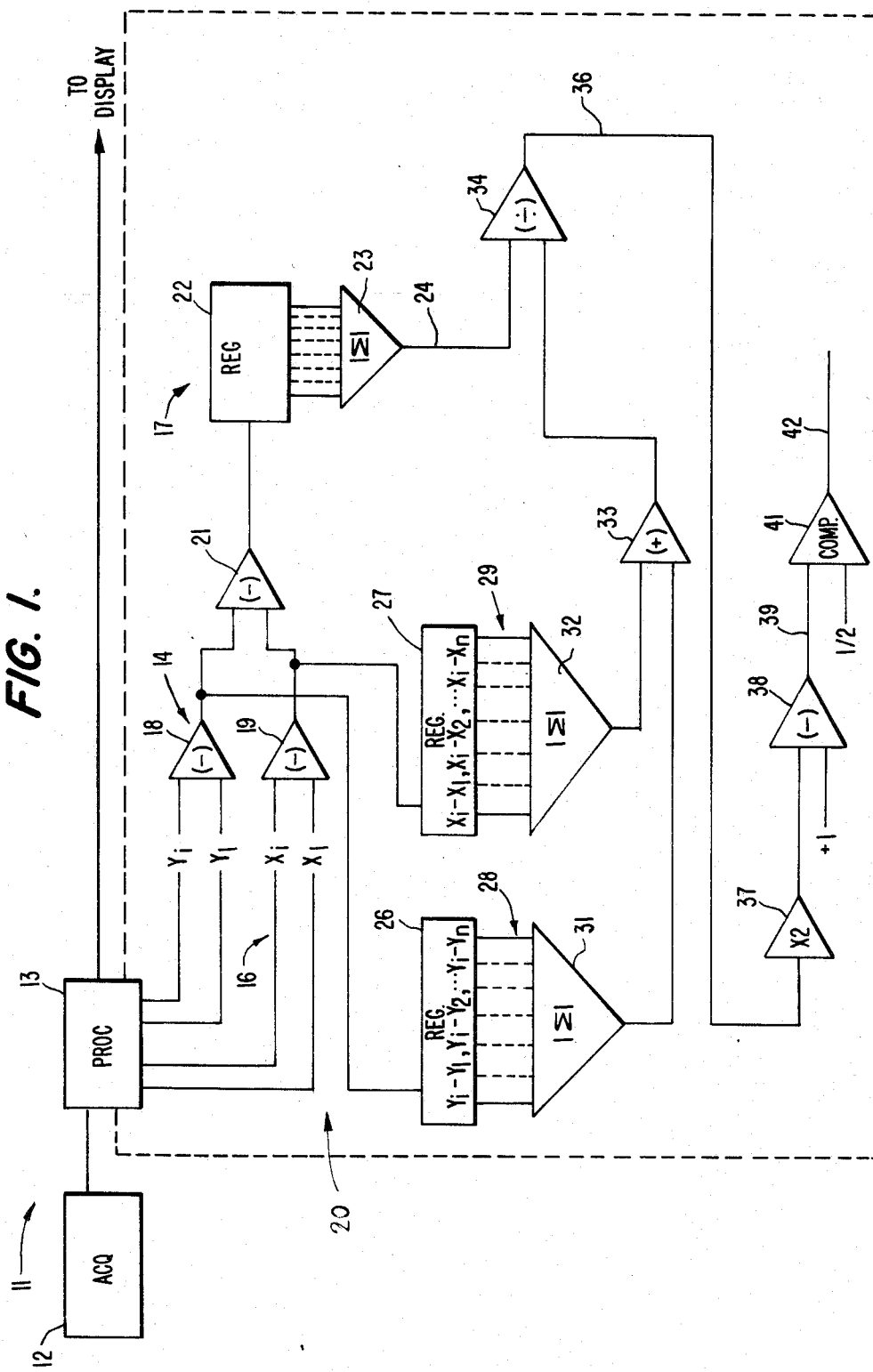
FIG. 1 is a block diagram showing of a pseudo-correlation determination system.

In FIG. 1 there is shown a block diagram of a pseudo-correlation determination system 11. The determination system comprises, for the purposes of demonstrating the invention and the inventive concepts discussed herein, an acquisition section 12 for acquiring data with which to generate a "shape" i.e. a graph. The acquired data is delivered to a processing section 13 for processing the data. The processing section 13 includes means for transferring data to correlation processing section 20. The section comprises means for the template data shown generally at 14, and means for processing the acquired data, shown generally at 16. In addition means 17 for combining the processed template data and the processed acquired data is provided.

Figure 3A:
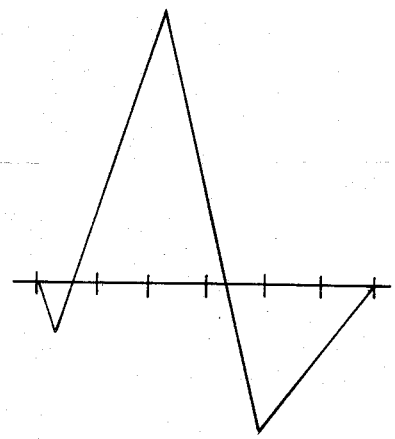

In the exemplary system for ECG data described herein, the template data comprises a typical characteristic QRS wave, such as shown in FIG. 3a. A number (N) of data points are selected which describe the characteristic shape of the QRS wave. The number is in this case eight (8). Thus the template data values Yi are for the N points 1 to 8. The data at these N points is stored in memory 15 and then used for the correlation.

The first operation on the template data is to subtract the data value of the first data point from the data value of each of the 8 points. This operation is indicated by the subtraction unit 18. The inputs of the subtraction unit are Yi and Y1, indicating that the first data point is subtracted from the value of each of the (N) data points, from 1 to 8 in this example.

In a similar manner, the first operation on the acquired data is the subtraction of the data at the first of point the selected subset of acquired data from the acquired data at each of the data points. This operation is indicated by subtraction unit 19. The differences obtained from units 18 and 19 are then used to obtain a new difference, indicated by unit 21. Unit 21 subtracts the differences of unit 18 from the differences of unit 19.

In one aspect of the invention, the subtractions performed by units 18 and 19 are done at the same time as the data is acquired. Thus in that aspect of the invention unit 21 takes the differences between the differences of unit 19 and unit 18 for each of the 8 data points.

Alternatively, a register or registers may be provided so that the units 18 and 19 are not required to perform substantially simultaneously. The output of unit 21 is inserted into register unit 22. Unit 22 registers the obsolute values of the differences obtained by unit 21. Thus the inputs to register unit 22, are the absolute values of the differences between the outputs of units 18 and 19 for the 8 points of interest. Means are provided for summing the values in register unit 22. More particularly, summing unit 23 provides at its output 24 the absolute sum of the values provided by unit 21, in this example eight.

The outputs of units 18 and 19 are also registered in registers 26 and 27 respectively. In this example each of the registers 26 and 27 have specific data values registered in them for each of the data points 1-8. The outputs of registers 26 and 27 appear on outputs 28 and 29 respectively. The outputs 28 and 29 each comprise a set of eight (8) data values without the negative or positive sign which are transmitted to summation circuits 31 and 32 respectively. The summation circuits provide absolute values at their output. The outputs of summation units 31 and 32 are added together in ADD unit 33.

Means are provided for dividing the output of the unit 23 by the output of the add unit 33. These means are shown as divide unit 34. The output of divide unit 34 on conductor 36 actually provides the correlation criteria required. However, means are provided for causing this output to be less than one. More particularly the output of unit 34 is multiplied by 2 in unit 37. Then the output of unit 37 is subtracted from plus one in unit 38. The output of unit 38 on conductor 39 is compared to a threshold value shown here as 0.5. A correlation signal indicating that there is correlation, appears at the output of unit 41 on conductor 42 if the value on conductor 39 is greater than 0.5. (That is, the quotient P is less than 0.25)

It should be understood that while specific block circuitry has been shown the psuedo-correlation can be determined in many other ways. In addition while a criteria of 0.5 has been discussed, different criteria can be used at different places in the block diagram to determine whether there is or is not a match between the template data and the acquired data.

Figure 2:
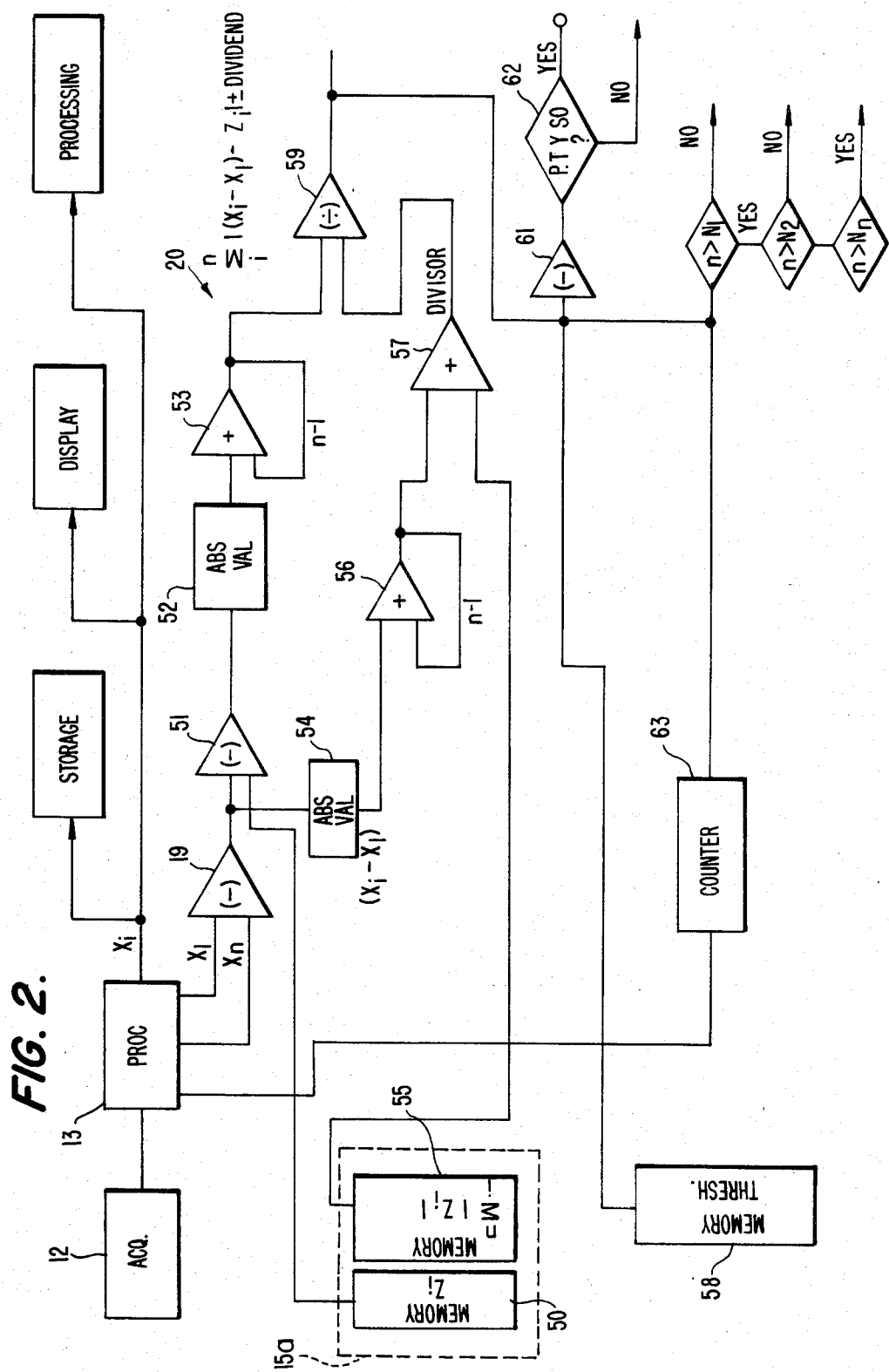
FIG. 2 is a block diagram of a preferred system for determining pseudo-correlation and FIGS. 3a, 3b, and 3c, are sample graphs, including a template, an acquired shape matching the template and an acquired shape not matching the template to demonstrate the operation of the correlation determination system as described.

FIG. 2 depicts the block diagram for a preferred embodiment of a circuit for calculating the quotient P of equation (2) and comparing it to a threshold T.

In this preferred embodiment, the data is acquired by acquisition unit 12, while the template processed data is already stored in memory 15a. The acquired data is processed by processor 13 which also transmits the data to be stored, to be displayed and/or to be processed by other means for other purposes. At the same time, processor 13 transmits each new data element to the psuedo-correlating circuits 20 to process the data for correlation purposes.

The first value in the data set X1 is subtracted by subtracting unit 19 from each element Xi in turn. It is shown subtracting the nth element Xn. The difference is then sent to two different places. Subtracting unit 51 subtracts from it the equivalent templated Zi, which was stored in Zi memory 50 of memory unit 15a. Unit 52 transforms the twice subtracted data to absolute values (usually by taking 2-s complements if the sign set is positive) and transfers it to summing unit 53. At the same time, unit 54 transfers the absolute values of the once-subtracted data to summing unit 56. The output of the summing unit is the sum of all data passing through it from the initiation of the summing process to the current value (in the example, the nth). The output of summing of unit 56 is added in adder 57 to the equivalent sum for the template, which was stored in $|Zi|$ memory 55 of unit 15a.

The output of summing unit 53 is the current dividend, and the output of adder 57 is the current divisor, which are divided in dividing unit 59 to yield the current quotient Pn which is sent on for further use. At the same time, it is subtracted in subtracting unit 61 from the current threshold Tn which was stored in memory unit 58, and the difference is checked in comparator 62 to determine whether it is positive (no match) or negative (match).

A counter 63 is then consulted, so that if n has reached a counter value of say N1, or N2, etc., decisions can be made. For example, if n has reached N/2 and the quotient P N/2 is still above a threshold T N/2 the process is stopped, a "no match" condition is declared and the process is renewed for a different subset. This decision mechanism further shortens the time necessary to determine the matching.

Figure 3B:
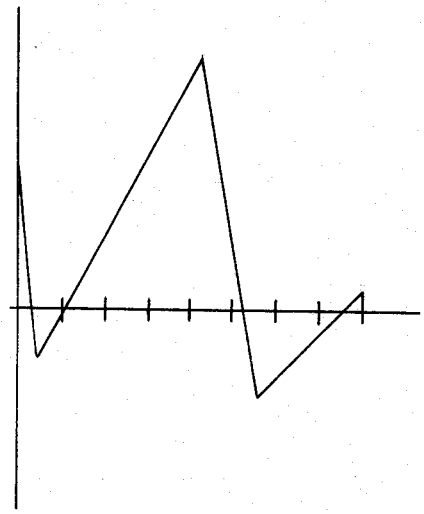
Figure 3C:
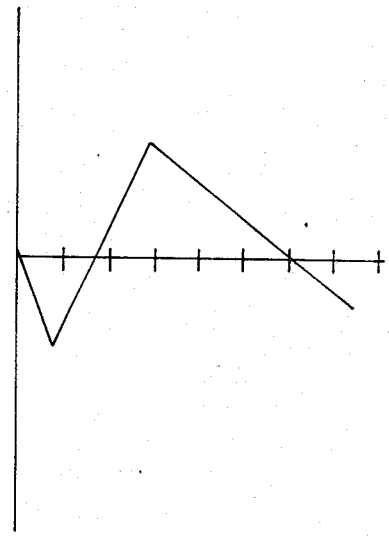

FIG. 3 shows graphs of examples of template data, acquired data I and acquired data II in FIGS. 3a, 3b and 3c, respectively to show how the psuedo-correlation technique and equipment are used to determine the correlation between template data and the acquired data I and between the template data and the acquired data II. Eight data points are used in each of the three example graphs. The value of the data at each of the data points is given in the following Table I. Thus the data for the template at the eight data points are shown in the first column of the table under Yi. The data for the graph of acquired data I is shown as XI in the second data column.

Similarly, the data of each of the data points in the third graph is shown in the column labelled X II. These data points are processed as has been described herein and as particularly shown in the following equation for psuedo-correlation, wherein:

$$r = 1 - 2*\frac{\sum_{i=2}^{8}|(Xi - X1) - (Yi - Y1)|}{\sum_{i=2}^{8}|Xi - X1| + \sum_{i=2}^{8}|Yi - Y1|} \tag{10}$$

The psuedo-correlation value obtained using the template of FIG. 3a and the graph of FIG. 3b comes out to 0.835 which indicates a match since any psuedo-correlation over 0.5 indicates a match. The psuedo-correlation value obtained from the template of FIG. 3a and the graph of FIG. 3c comes to 0.033 (see table 1) which indicates that there is no match since any value under 0.5 is indicative of no correlation.

These results are in complete agreement, by the way, with the results obtained by the tedious calculation of linear correlations. The linear correlations of template 3A and data 3B is R=0.991 which indicates a match. The linear correlation of template 3A with data 3C is R=0.581, which indicates no match, as the threshold is usually in the range of T=0.8−0.9.

One of the features of the psuedo-correlation determination is that the computation can be made during the process, since there are no averages required and the computation process is much faster because there are no square root determinations required. Also, if at any time during the processing no matching is indicated there is no need to proceed, thereby effecting a further valuable time saving. For example, after only five steps it is easily seen (without interrupting the calculation, if it needs to continue) that the data set of 3B has a psuedo-correlation with the template of 3A of r=0.888, while the data set of 3C has a psuedo-correlation of r=0.205. There is therefore no need to continue calculating the psuedo-correlation of the set 3C. Such a mid-way decision using the prior art linear correlation method does not save any computation time as it cannot be done using the partially summed data, but must be done in addition. The additional computation overwhelms the savings.

TABLE I

| Data Point | Yi | XI | XII | XI-X1 | XIIi-X1 | Yi-Y1 | Dividend | Divisor | Quot (P) | Pseudo Corr. (r) |
|---|---|---|---|---|---|---|---|---|---|---|
| 1 | 0 | 0 | 0 | 0 | 0 | 0 | | | | |
| 2 | −1 | 0 | −6 | 0 | −6 | −1 | | | | |
| 3 | +1 | 0 | +6 | 0 | +6 | +1 | | | | |
| 4 | +14 | +16 | +17 | +16 | +17 | +14 | | | | |
| 5 | +29 | +28 | +9 | +28 | +9 | +29 | | | | |
| 6 | +10 | +9 | +6 | +9 | +6 | +10 | | | | |
| 7 | −10 | −9 | +4 | −9 | +4 | −10 | | | | |
| 8 | −5 | −1 | +2 | −1 | +2 | −5 | | | | |
| Graph FIG. 3b | | | | | | | 11 | 133 | .083 | 0.835 |
| Graph FIG. 3a | | | | | | | 58 | 120 | .483 | 0.033 |

While methods and systems are herein described using preferred embodiments it should be evident to those skilled in the art that the invention can be implemented in many other ways without the departing from the scope of the invention.

What is claimed is:

1. A method of determining whether a first shape defined by a first plurality of data matches a predetermined shape, said method comprising the steps of:
    obtaining a selected set of data values (Yi) at a plurality of data points N describing said pre-determined shape,
    obtaining a first set of data values from said first plurality of data using at least the same number of data points as said plurality of data points,
    obtaining a sub-set of data values (Xi) from said first set of data values using said same number N of data points,
    selecting a fiducial value from said selected set of data values and said sub-set of data values, computing a quotient from a dividend and a divisor consisting of summation of differences obtained using said data values from said selected set of data values, said sub-set of data values and said fiducial values, and
    using said quotient to determine whether said first shape matches said pre-determined shape.

2. The method of claim 1 wherein a plurality of pre-determined shapes are used and the method is for determining whether a first shape defined by the first plurality of data matches any of said pre-determined shapes, said method comprising the steps of:
    obtaining a selected set of data values Yji at a number of data points N for describing each of said pre-determined shapes, the number N being the same for each of said pre-determined shapes,
    computing a plurality of quotients from dividends and divisors consisting of summations of differences obtained using the plurality of data values from said plurality of selected sets of data values, said subset of data values and said fiducial values, and
    using said plurality of quotients to determine which of said pre-determined shapes is matched by said first shape.

3. The method of claim 1 wherein said first shape includes a plurality of first shapes, said method comprising the steps of:
    obtaining a plurality of first sets of data values from said first plurality of data,
    obtaining a plurality of subsets of data values Xji from said first set of data values using the same number N of data points,
    computing a plurality of quotients from dividends and divisors consisting of summations of differences obtained using data values from said selected set of data values, said plurality of subsets of data values and said fiducial values, and
    using said plurality of quotients to determine which of said first shapes, if any, matches said pre-determined shape.

4. The method of claim 1 wherein said fiducial value is the value of the data at a selected data point in said selected set of data values and in said subset of data values.

5. The method of claim 1 wherein said fiducial value is the value of the data at the first data point in said selected set of data values and in said subset of data values.

6. The matching method of claim 1 including the steps of:
    multiplying said quotient by 2 to obtain a product,
    subtracting said product from 1, and
    using the difference to compare to a threshold for determining whether said first shape matches said pre-determined shape.

7. The method of claim 1 wherein said dividend comprises the summation of the absolute value of the differences between the values of the data in said first set of data values and the data value at said first data point in said first set, minus the differences between the values of the data in said selected set of data values and the data value at said first data point in said selected set, and wherein the divisor comprises the summation absolute values of the differences between the data value of the data points of the first set minus the value of the data at the first point plus the summation of the values of the data at the data points of the selected set of data values minus the value at the first data point of the selected set.

8. The method of claim 7 wherein the dividend is the summation of the absolute values of the the differences between each of the data values in the subset at each of the data points and each of the data values at the same data points on the selected set of data minus the differences between the data value at the first data point of the subset and the data value of the selected set at the first data point.

9. The method of claim 8 wherein the quotient is multiplied by 2 and subtracted from 1 to obtain a first difference and using the first difference to compare to a threshold level to determine matching.

10. The method of claim 1 wherein said selected set of data values is taken from the acquired data.

11. The method of claim 10 wherein said selected set of data values defining said pre-determined shape is updated.

12. The method of claim 11 including obtaining the selected set of data values defining a pre-determined shape from said first plurality of data and updating said shape by adding more data values to said selected set of data values.

13. The method of claim 9 wherein the quotient comprises the summation of the absolute value of the data values at each of the data points in said subset minus the data value of the first data point in said subset minus the quantity $Z_i$; divided by the summation of the absolute value of the first plurality of data values at each of said data points minus the value at the first data point of the first plurality of data and the quantity Z added to the last summation; where the quantity $Z_i$ equals the values $Y_i$ at each of the data points in the selected set of data values minus the data value $Y_1$ in the selected set of data values at the first data point; and where the quantity Z equals the summation of the absolute value of the differences between the values $Y_i$ in the selected set of data at said data points minus the value $Y_1$ at the first data point.

14. The method of claim 1 wherein said first plurality of data comprises acquired data.

15. The method of claim 1 wherein said first plurality of data comprises processed acquired data.

16. A system for determining whether a first shape defined by a first plurality of data matches a pre-determined shape, said system comprising:
means for obtaining a selected set of data values ($Y_i$) at a plurality of data points N describing said pre-determined shape, means for obtaining a first set of data values from said first plurality of data using at least the same number of data points as said plurality of data points,
means for obtaining a sub-set of data values ($X_i$) from said first set of data values using said same number N of data points,
means for selecting a fiducial value from said selected set of data values and said sub-set of data values,
means for computing a quotient from a dividend and a divisor consisting of summations of differences obtained using said data values from said selected set of data values, said sub-set of data values and said fiducial values, and
means for using said quotient to determine whether said first shape matches said predetermined shape.

17. The system of claim 16 wherein a plurality of pre-determined shapes are used and the system is for determining whether a first shape defined by the first plurality of data matches any of said pre-determined shapes, said system comprising:
means for obtaining a selected set of data values $Y_{ji}$ at a number of data points for describing each of said pre-determined shapes, the number N being the same for each of said pre-determined shapes,
means for computing a plurality of quotients from dividends and divisors consisting of summations of differences obtained using the plurality of data values from said plurality of selected sets of data values, said subset of data values and said fiducial values, and
means for using said plurality of quotients to determine which of said pre-determined shapes is matched by said first shape.

18. The system of claim 16 wherein said first shape includes a plurality of first shapes, said system comprising:
means for obtaining a plurality of first sets of data values from said first plurality of data,
means for obtaining a plurality of subsets of data values $X_{ji}$ from said first set of data values using the same number N of data points,
means for computing a plurality of quotients from dividends and divisors consisting of summations of differences obtained using data values from said first set of data values, said plurality of subsets of data values and said fiducial values, and
means for using said plurality of quotients to determine whice of said first shapes, if any, matches said predetermined shape.

19. The system of claim 16 wherein said fiducial value is the value of the data at a selected data point in said selected set of data values and in said subset of data values.

20. The system of claim 16 wherein said fiducial value is the value of the data at the first data point in said selected set of data values and in said subset of data values.

21. The matching system of claim 16 including:
means for multiplying said quotient by 2 to obtain a product,
means for subtracting said product from 1, and
means for using the difference to compare to a threshold for determining said first shape matches said predetermined shape.

22. The system of claim 16 wherein said dividend comprises the summation of the absolute value of the differences between the values at the data points of the first set of data and the value of the data at the first data point of the first set of data, minus the differences between the values at the data points of the selected set and the value of the first data point of said selected set, and wherein the divisor comprises the summation of the absolute values of the differences between the data values of the first set and the value of the data of the first set at the first point plus the summation of the absolute values of the differences between the values of the selected data at said first data point.

23. The system of claim 22 wherein the dividend is the summation of absolute values of the the differences between each of the data values of the subset at each of the data points and each of the data values at same data points on the selected set of data minus the differences between the data value at the first data point of the subset and the data value of the selected set at the first data point.

24. The system of claim 23 wherein the quotient is multiplied by 2 and subtracted from 1 to obtain a first difference, and means for using the first difference to compare to a threshold level to determine matching.

25. The system of claim 16 wherein said selected set of data values is taken from the acquired data.

26. The system of claim 25 wherein said selected set of data values defining said pre-determined shape is updated.

27. The system of claim 24 including means for obtaining the selected set of data values defining a predetermined shape from said first plurality of data, updating said shape by adding more data values to said selected set of data values.

28. The system of claim 24 wherein the quotient comprises the summation of the absolute values of the differences of the data values at each of the data points in said subset minus the data value of the first data point in said subset, minus the quantity $Z_i$; divided by the summation of the absolute values of the differences of the data values at each of the data points in said subset minus the data value of the first data point in said subset, plus the quantity Z; where the quantity $Z_i$ equals the values of each of the data points in the selected set of data values minus the value Y1 in the selected set of data values at the first data point; and where the quantity Z equals the summation of the absolute values of the differences between the values $Y_i$ in the selected set of data at said data points minus the value Y1 at the first data point.

29. The system of claim 16 wherein said first plurality of data comprises acquired data.

30. The system of claim 16 wherein said first plurality of data comprises processed acquired data.

* * * * *